(12) United States Patent
Chen et al.

(10) Patent No.: US 11,369,648 B2
(45) Date of Patent: Jun. 28, 2022

(54) PROBIOTIC MIXED PREPARATION WITH ANTI-INFLUENZA ABILITY AND APPLICATION THEREOF

(71) Applicant: Jiangnan University, Wuxi (CN)

(72) Inventors: Wei Chen, Wuxi (CN); Wenwei Lu, Wuxi (CN); Qixiao Zhai, Wuxi (CN); Xinyang Liu, Wuxi (CN); Jianxin Zhao, Wuxi (CN); Feng Hang, Wuxi (CN); Hao Zhang, Wuxi (CN)

(73) Assignee: JIANGNAN UNIVERSITY, Wuxi (CN)

(*) Notice: Subject to any disclaimer, the term of this patent is extended or adjusted under 35 U.S.C. 154(b) by 26 days.

(21) Appl. No.: 16/892,404

(22) Filed: Jun. 4, 2020

(65) Prior Publication Data

US 2020/0368297 A1  Nov. 26, 2020

Related U.S. Application Data

(63) Continuation of application No. PCT/CN2019/082656, filed on Apr. 15, 2019.

(30) Foreign Application Priority Data

Dec. 26, 2018 (CN) .......................... 201811598890.5

(51) Int. Cl.
| | | |
|---|---|---|
| *A61K 35/747* | (2015.01) | |
| *A23L 33/135* | (2016.01) | |
| *A61P 31/16* | (2006.01) | |
| *A61K 35/745* | (2015.01) | |

(52) U.S. Cl.
CPC .......... *A61K 35/747* (2013.01); *A23L 33/135* (2016.08); *A61K 35/745* (2013.01); *A61P 31/16* (2018.01); *A23Y 2220/00* (2013.01); *A23Y 2300/29* (2013.01)

(58) Field of Classification Search
None
See application file for complete search history.

(56) References Cited

U.S. PATENT DOCUMENTS

2008/0274162 A1    11/2008   Nessa et al.

FOREIGN PATENT DOCUMENTS

| CN | 1109763 A | 10/1995 |
|---|---|---|
| CN | 101031313 A | 9/2007 |
| CN | 108653574 A | 10/2018 |
| CN | 108949640 A | 12/2018 |
| CN | 109069558 A | 12/2018 |
| CN | 109576185 A | 4/2019 |
| WO | 2018109730 A1 | 6/2018 |

OTHER PUBLICATIONS

PCT/CN2019/082656 ISR ISA210 dated Sep. 17, 2019.

*Primary Examiner* — Oluwatosin A Ogunbiyi
(74) *Attorney, Agent, or Firm* — IPro, PLLC

(57) ABSTRACT

The disclosure discloses a probiotic mixed preparation with anti-influenza ability and application thereof, and belongs to the technical fields of microorganisms and medicines. The probiotic mixed preparation has anti-influenza effects, which are embodied in: (1) significantly reducing the degree of weight loss of influenza mice; (2) significantly improving the blood indexes of the influenza mice; (3) significantly improving the inflammation status of respiratory tract infections in the influenza mice; (4) significantly reducing the viral load in the lungs of the influenza mice (i.e., significantly inhibiting the replication and multiplication of influenza viruses in the influenza mice); and (5) significantly increasing the expression quantity of antiviral protein MxA in the lungs of the influenza mice. Therefore, the probiotic mixed preparation has great application prospects in preparation of a product for preventing and/or treating atopic dermatitis and even preventing and/or treating influenza.

8 Claims, 8 Drawing Sheets
Specification includes a Sequence Listing.

SEQUENCE LISTING

<160> NUMBER OF SEQ ID NOS: 2

<210> SEQ ID NO 1
<211> LENGTH: 1437
<212> TYPE: DNA
<213> ORGANISM: Lactobacillus mucosae

<400> SEQUENCE: 1

```
agtcgaacgc gttggcccaa ctgattgaac gtgcttgcac ggacttgacg ttggtttacc      60
agcgagtggc ggacgggtga gtaacacgta ggtaacctgc cccaaagcgg gggataacat     120
ttggaaacag atgctaatac cgcataacaa tttgaatcgc atgattcaaa tttaaaagat     180
ggcttcggct atcactttgg gatggacctg cggcgcatta gcttgttggt agggtaacgg     240
cctaccaagg ctgtgatgcg tagccgagtt gagagactga tcggccacaa tggaactgag     300
acacggtcca tactcctacg ggaggcagca gtagggaatc ttccacaatg ggcgcaagcc     360
tgatggagca acaccgcgtg agtgaagaag ggtttcggct cgtaaagctc tgttgttaga     420
gaagaacgtg cgtgagagca actgttcacg cagtgacggt atctaaccag aaagtcacgg     480
ctaactacgt gccagcagcc gcggtaatac gtaggtggca agcgttatcc ggatttattg     540
ggcgtaaagc gagcgcaggc ggtttgataa gtctgatgtg aaagcctttg gcttaaccaa     600
agaagtgcat cggaaactgt cagacttgag tgcagaagag gacagtggaa ctccatgtgt     660
agcggtggaa tgcgtagata tatggaagaa caccagtggc gaaggcggct gtctggtctg     720
caactgacgc tgaggctcga aagcatgggt agcgaacagg attagatacc ctggtagtcc     780
atgccgtaaa cgatgagtgc taggtgttgg agggtttccg cccttcagtg ccgcagctaa     840
cgcattaagc actccgcctg gggagtacga ccgcaaggtt gaaactcaaa ggaattgacg     900
ggggcccgca caagcggtgg agcatgtggt ttaattcgaa gctacgcgaa gaaccttacc     960
aggtcttgac atcttgcgcc aaccctagag atagggcgtt ccttcggga acgcaatgac    1020 aggtggtgca tggtcgtcgt cagctcgtgt cgtgagatgt tgggttaagt cccgcaacga    1080
gcgcaaccct tgttactagt tgccagcatt cagttgggca ctctagtgag actgccggtg    1140
acaaaccgga ggaaggtggg gacgacgtca gatcatcatg cccttatga cctgggctac    1200 acacgtgcta caatggacgg tacaacgagt cgcgaactcg cgagggcaag ctaatctctt    1260
```

```
aaaaccgttc tcagttcgga ctgcaggctg caactcgcct gcacgaagtc ggaatcgcta    1320
gtaatcgcgg atcagcatgc cgcggtgaat acgttcccgg gccttgtaca caccgcccgt    1380
cacaccatga gagtttgcaa cacccaaagt cggtggggta acccttcggg gagctag      1437

<210> SEQ ID NO 2
<211> LENGTH: 1395
<212> TYPE: DNA
<213> ORGANISM: Bifidobacterium breve

<400> SEQUENCE: 2
caagtcgaac gggatccatc gggctttgcc tggtggtgag agtggcgaac gggtgagtaa      60
tgcgtgaccg acctgcccca tgcaccggaa tagctcctgg aaacgggtgg taatgccgga     120
tgctccatct caccgcatgg tgttttggga aagcctttgc ggcatgggat ggggtcgcgt     180
cctatcagct tgatggcggg gtaacggccc accatggctt cgacgggtag ccggcctgag     240
agggcgaccg gccacattgg gactgagata cggcccagac tcctacggga ggcagcagtg     300
gggaatattg cacaatgggc gcaagcctga tgcagcgacg ccgcgtgagg gatggaggcc     360
ttcgggttgt aaacctcttt tgttagggag caaggcattt tgtgttgagt gtacctttcg     420
aataagcacc ggctaactac gtgccagcag ccgcggtaat acgtagggtg caagcgttat     480
ccggaattat tgggcgtaaa gggctcgtag gcggttcgtc gcgtccggtg tgaaagtcca     540
tcgcttaacg gtggatccgc gccgggtacg ggcgggcttg agtgcggtag gggagactgg     600
aattcccggt gtaacggtgg aatgtgtaga tatcgggaag aacaccaatg gcgaaggcag     660
gtctctgggc cgttactgac gctgaggagc gaaagcgtgg ggagcgaaca ggattagata     720
ccctggtagt ccacgccgta aacggtggat gctggatgtg gggcccgttc cacgggttcc     780
gtgtcggagc taacgcgtta agcatcccgc ctggggagta cggccgcaag gctaaaactc     840
aaagaaattg acgggggccc gcacaagcgg cggagcatgc ggattaattc gatgcaacgc     900
gaagaacctt acctgggctt gacatgttcc cgacgatccc agagatgggg tttcccttcg     960
gggcgggttc acaggtggtg catggtcgtc gtcagctcgt gtcgtgagat gttgggttaa    1020
gtcccgcaac gagcgcaacc ctcgccccgt gttgccagcg gattgtgccg ggaactcacg    1080
ggggaccgcc ggggttaact cggaggaagg tgggatgac gtcagatcat catgcccctt     1140
acgtccaggg cttcacgcat gctacaatgg ccggtacaac gggatgcgac agcgcgagct    1200
ggagcggatc cctgaaaacc ggtctcagtt cggatcgcag tctgcaactc gactgcgtga    1260
aggcggagtc gctagtaatc gcgaatcagc aacgtcgcgg tgaatgcgtt cccgggcctt    1320
gtacacaccg cccgtcaagt catgaaagtg ggcagcaccc gaagccggtg gcctaacccc    1380
ttgcgggagg gagcc                                                    1395
```

PROBIOTIC MIXED PREPARATION WITH ANTI-INFLUENZA ABILITY AND APPLICATION THEREOF

TECHNICAL FIELD

The disclosure relates to a probiotic mixed preparation with anti-influenza ability and application thereof, and belongs to the technical fields of microorganisms and medicines.

BACKGROUND

Influenza is often pandemic in autumn and winter and is mainly caused by influenza viruses. Influenza viruses can be divided into three types: influenza virus A, influenza virus B, and influenza virus C. Human influenza is mainly caused by influenza virus A and influenza virus B. In general, animal influenza viruses do not infect humans, and human influenza viruses do not infect animals, but pigs are the exception. Pigs can be infected with both avian influenza viruses and human influenza viruses, but mainly the avian influenza viruses. However, once pigs are infected with the avian influenza viruses, the avian influenza viruses can be easily transmitted to humans, causing a human influenza pandemic, for example, the "Spanish Flu" that occurred in 1819-1920.

"Spanish Flu" is the most serious influenza pandemic in the history of the world, covering a wide range, with a clinical incidence of up to 40%, accompanied by various types of complications of pneumonia, and causing 20-40 million deaths which far exceeds World War I. Restricted by scientific and technical conditions, people were unable to isolate the causative agent of "Spanish Flu" at that time. Until 1997, American scientists published in Science that the 1918 influenza virus was very similar to the swine influenza virus, and is a virus closely related to the influenza virus A (H1N1).

In the following nearly one hundred years, there were still many influenza pandemics in the world, causing human suffering and economic loss to varying degrees. It can be said that since the emergence of influenza, it has not been able to be completely controlled, showing intermittent outbreaks.

One of the main reasons that influenza cannot be completely controlled is that although most influenza viruses are not heat-resistant, and they can be inactivated by heating at 56° C. for 30 minutes and will soon lose the infectivity at room temperature, however, the influenza virus has high degree of mutation. Among them, the most frequently mutated should be influenza virus A, and a large antigenic mutation occurs every ten years, resulting in a new virus strain. Such change is called an antigenic shift/qualitative change in the antigen. Small mutations in antigens also occur within influenza virus subtypes, mainly point mutations in the amino acid sequence of the antigen, called antigenic drift/quantitative change in the antigen, which prevents people from having a long-term effective vaccine against influenza.

Studies on the pathogenic mechanism of influenza virus in the medical field have long been carried out. Animal experiments have shown that there are multiple pathogenic pathways that can induce respiratory infections, which in turn cause severe respiratory diseases. The inflammation caused by the respiratory diseases is mainly concentrated in the lungs of animals and manifests in the form of pneumonia. For example, histopathological examination of the lungs of mice with respiratory infection can reveal damage to the alveolar structure of the mice, ruptured lung septum, necrosis and shedding of alveolar epithelial cells, and other pathological changes; the lung tissues of a small number of mice show widening of the lung septum; and the lung tissues with local lesion of the mice show epithelial hyperplasia.

Currently, the World Health Organization believes that vaccination every year before the peak of the influenza epidemic is the most effective means of prevention. At the present stage, there are two types of trivalent influenza vaccines that have been marketed: Inactivated Influenza Vaccine (IIV) and Live Attenuated Influenza Vaccine (LAIV), consisting of three viruses including 2 influenza virus A strains and 1 influenza virus B strain. There are mainly two types of western medicines for the treatment of influenza infections, one is neuraminidase inhibitors such as oseltamivir, zanamivir and peramivir, the mechanism of which is that the glycoprotein neuraminidase acting on the surface of the virus prevents the virus particles from invading human cells; the other is M2 ion channel blockers such as amantadine and rimantadine, which act on the proton channel M2 protein and inhibit the protein ion channel to inhibit the replication of influenza virus A.

However, vaccination cannot effectively protect the body from virus infection for a long time, and drug treatment has side effects on the central nervous system while killing the virus. Therefore, there is still a need for a drug or a treatment method that can effectively protect the body from influenza virus infection for a long time and alleviate some clinical symptoms of influenza, while not bringing side effects to the central nervous system of patients.

In recent years, a large number of studies have shown that intestinal microorganisms play an important role in maintaining human health. At the same time, the effects of probiotics on health in human intervention studies include improving children's acute diarrhea, alleviating milk allergy and atopic dermatitis in children, and alleviating irritable bowel syndrome in humans. In addition, probiotics may have effects through the intestinal mucosa, and balance the local microflora by inhibiting the growth of pathogenic microorganisms, thereby enhancing local and systemic immune responses. In addition, probiotics may affect the composition and activity of the microflora in the intestinal contents. It has also been reported that influenza caused by virus can affect the structure of the intestinal flora, and specific probiotics can effectively reduce the duration and severity of acute rotavirus gastroenteritis. Therefore, it is possible to start with intestinal microorganisms and try to find new drugs or new methods to prevent and treat influenza, so as to overcome the shortcomings of obvious side effects of existing treatment drugs and treatment methods.

SUMMARY

To solve the above problems, the disclosure provides a probiotic mixed preparation containing *Lactobacillus mucosae* GDMCC60460 and *Bifidobacterium breve* CCFM1026. The probiotic mixed preparation has anti-influenza effects, which are embodied in: (1) significantly reducing the degree of weight loss of influenza mice; (2) significantly improving the blood indexes of the influenza mice; (3) significantly improving the inflammation status of respiratory infections in the influenza mice; (4) significantly reducing the viral load in the lungs of the influenza mice (i.e., significantly inhibiting the replication and multiplication of influenza viruses in the influenza mice); and (5) significantly increasing the expression quantity of antiviral protein MxA in the lungs of the influenza mice. Therefore, the probiotic mixed preparation has great application prospects in preparation of a product for preventing and/or treating atopic dermatitis and even preventing and/or treating influenza.

The disclosure has the technical solutions as follows:

The disclosure provides a probiotic mixed preparation with anti-influenza ability, and the probiotic mixed preparation contains *L. mucosae* GDMCC60460 and *B. breve* CCFM1026.

The *L. mucosae* GDMCC60460 was preserved at Guangdong Microbial Culture Collection Center on Oct. 11, 2018, with the preservation number GDMCC No. 60460, and the preservation address is 5th Floor, Building 59, Grand Courtyard 100, Xianlie Middle Road, Guangzhou.

The *B. breve* CCFM1026 was preserved at the Guangdong Microbial Culture Collection Center on Oct. 11, 2018, with the preservation number GDMCC No. 60459, and the preservation address is 5th Floor, Building 59, Grand Courtyard 100, Xianlie Middle Road, Guangzhou.

The *L. mucosae* GDMCC60460 is isolated from human feces. By sequencing analysis, the 16S rRNA sequence of the strain is shown in SEQ ID NO. 1. By comparing the sequence in GenBank, the results show that the strain is *L. mucosae* and is named as *L. mucosae* GDMCC60460.

The *L. mucosae* GDMCC60460 has short rod-shaped bacterial cells and round, rough and transparent colonies; grows at 45° C. and does not grow at 15° C.; reaches a stationary phase after being cultured in an MRS liquid medium at 37° C. for 12 hours; performs heterofermentation, and produces acid and gas from glucose.

The *B. breve* CCFM1026 is isolated from a human feces sample. By sequencing analysis, the 16S rRNA sequence of the strain is shown in SEQ ID NO. 2. The sequence is compared in GenBank, and the results show that the query cover between the strain and *B. breve* is 100% and the identity (Ident) is 99%, therefore, the strain is determined to be *B. breve* and named as *B. breve* CCFM1026.

The *B. breve* CCFM1026 has short rod-shaped bacterial cells, is Gram-positive, is irregularly stained with methylene blue staining, has no spores, flagella and capsules, does not move; has round white colonies; reaches a stationary phase after being cultured at 37° C. under anaerobic conditions for 30 h, and uses glucose for atypical heterolactic fermentation.

In an embodiment of the disclosure, the viable count of *L. mucosae* GDMCC60460 in the probiotic mixed preparation is not less than $1 \times 10^6$ CFU/mL; and the viable count of *B. breve* CCFM1026 in the probiotic mixed preparation is not less than $1 \times 10^6$ CFU/mL.

The disclosure provides application of the probiotic mixed preparation in preparation of a product for preventing and/or treating influenza.

In an embodiment of the disclosure, in the product, the viable count of *L. mucosae* GDMCC60460 is not less than $1 \times 10^6$ CFU/mL; and the viable count of *B. breve* CCFM1026 is not less than $1 \times 10^6$ CFU/mL.

In an embodiment of the disclosure, the product includes food, medicine or health food.

In an embodiment of the disclosure, the medicine contains the probiotic mixed preparation, a pharmaceutical carrier and/or a pharmaceutical excipient.

In an embodiment of the disclosure, the food includes a dairy product, a bean product or a fruit and vegetable product produced by using a fermentation agent containing the probiotic mixed preparation; or the food includes a solid beverage containing the probiotic mixed preparation.

The disclosure provides a product for preventing and/or treating influenza, and the product contains the probiotic mixed preparation with anti-influenza ability.

In an embodiment of the disclosure, in the product, the viable count of *L. mucosae* GDMCC60460 is not less than $1 \times 10^6$ CFU/mL; and the viable count of *B. breve* CCFM1026 is not less than $1 \times 10^6$ CFU/mL.

In an embodiment of the disclosure, the product includes food, medicine or health food.

In an embodiment of the disclosure, the medicine contains the probiotic mixed preparation, a pharmaceutical carrier and/or a pharmaceutical excipient.

In an embodiment of the disclosure, the food includes a dairy product, a bean product or a fruit and vegetable product produced by using a fermentation agent containing the probiotic mixed preparation; or the food includes a solid beverage containing the probiotic mixed preparation.

In an embodiment of the disclosure, a preparation method of the fermentation agent is: inoculating *B. breve* CCFM1026 into a medium at an inoculation amount of 5-8% of the total mass of the medium, and performing culturing in an anaerobic environment of 37° C. for 30 h to obtain a culture solution; centrifuging the culture solution to obtain bacterial cells; washing the bacterial cells 2-4 times with a phosphate buffer solution with a pH of 7.2, and then performing resuspending with a 100 g/L trehalose freeze-drying protectant to obtain a resuspension solution; freeze-drying the resuspension solution by vacuum freezing to obtain *B. breve* CCFM1026 bacterial powder;

inoculating *L. mucosae* GDMCC60460 into a medium at an inoculation amount of 5-8% of the total mass of the medium, and performing culturing at 37° C. for 18 h to obtain a culture solution; centrifuging the culture solution to obtain bacterial cells; washing the bacterial cells 2-4 times with a phosphate buffer solution with a pH of 7.2, and then performing resuspending with a 100 g/L trehalose freeze-drying protectant to obtain a resuspension solution; freeze-drying the resuspension solution by vacuum freezing to obtain *L. mucosae* GDMCC60460 bacterial powder; and mixing the obtained *L. mucosae* GDMCC60460 bacterial powder and the *B. breve* CCFM1026 bacterial powder to obtain the fermentation agent;

wherein the mass ratio of the freeze-drying protectant to the bacterial cells is 2:1.

In an embodiment of the disclosure, the pH of the medium is 6.8.

In an embodiment of the disclosure, the protectant contains 100 g/L of skimmed milk powder, 150 g/L of trehalose and 10 g/L of sodium L-glutamate.

Beneficial Effects:

The disclosure provides a probiotic mixed preparation containing *L. mucosae* GDMCC60460 and *B. breve* CCFM1026. The probiotic mixed preparation has anti-influenza effects, which are embodied in:

(1) significantly reducing the degree of weight loss of influenza mice;

(2) significantly improving the blood indexes of the influenza mice;

(3) significantly improving the inflammation status of respiratory infections in the influenza mice;

(4) significantly reducing the viral load in the lungs of the influenza mice (i.e., significantly inhibiting the replication and multiplication of influenza viruses in the influenza mice); and (5) significantly increasing the expression quantity of antiviral protein MxA in the lungs of the influenza mice.

Therefore, the probiotic mixed preparation has great application prospects in preparation of a product for preventing and/or treating atopic dermatitis and even preventing and/or treating influenza.

Preservation of Biological Materials

*L. mucosae* GDMCC60460, with the taxonomic name of *L. mucosae*, was preserved at Guangdong Microbial Culture Collection Center on Oct. 11, 2018, with the preservation number GDMCC No. 60460, and the preservation address is 5th Floor, Building 59, Grand Courtyard 100, Xianlie Middle Road, Guangzhou.

*B. breve* CCFM1026, with the taxonomic name of *B. breve*, was preserved at the Guangdong Microbial Culture Collection Center on Oct. 11, 2018, with the preservation number GDMCC No. 60459, and the preservation address is 5th Floor, Building 59, Grand Courtyard 100, Xianlie Middle Road, Guangzhou.

DETAILED DESCRIPTION

Figure 1:
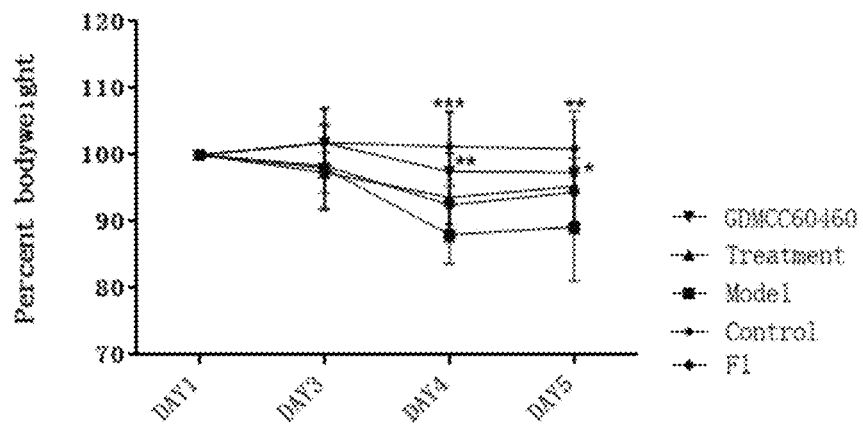
FIG. 1 shows comparison of body weight changes of different groups of influenza mice (*L. mucosae*).

Media Involved in the Following Examples are as Follows:

MRS plate (g/L): peptone 10 g/L, beef extract 10 g/L, glucose 20 g/L, sodium acetate 2 g/L, yeast powder 5 g/L, diammonium hydrogen citrate 2 g/L, $K_2PO_4 \cdot 3H_2O$ 2.6 g/L, $MgSO_4 \cdot 7H_2O$ 0.1 g/L, $MnSO_4$ 0.05 g/L, Tween 80 1 ml/L, agar 20 g/L, and cysteine hydrochloride 0.5 g/L.

EXAMPLE 1-1

Screening and Identification of *L. mucosae*

1. Screening

Human feces was used as a sample. After being pretreated, the sample was stored in about 20% glycerol in a refrigerator at −80° C. After being taken out and thawed, the sample was mixed, and 0.5 mL of the sample was pipetted and added to 4.5 mL. The sample was subjected to gradient dilution with 0.9% normal saline containing 0.05% cysteine. An appropriate gradient diluent was selected and coated on an MRS plate supplemented with 0.05% cysteine, and was cultured at 37° C. for 48 h. Typical colonies were selected and streaked on the MRS plate for purification. Single colonies were selected and transferred to a liquid MRS medium (containing 0.05% cysteine) for enrichment culture. The bacteria were preserved in 30% glycerol to obtain a strain GDMCC60460 and a strain F1.

2. Identification

The genomes of the GDMCC60460 and the F1 were extracted. The 16S rDNAs of the GDMCC60460 and the F1 were subjected to amplification and sequencing (Shanghai Sangon Biotech Co., Ltd.). The sequences were compared in GenBank, and the results showed that the strains were *L. mucosae* and were named as *L. mucosae* GDMCC60460 and *L. mucosae* F1.

EXAMPLE 1-2

Culture of *L. mucosae*

The *L. mucosae* GDMCC60460 was inoculated into an MRS solid medium (containing 0.05% cysteine) and cultured at 37° C. for 48 h. The colonies were observed and the bacterial cells were observed under a microscope. It was found that the colonies were round, rough and transparent, and the bacterial cells were short rod-shaped.

The *L. mucosae* GDMCC60460 was inoculated into an MRS medium (containing 0.05% cysteine) and cultured at 37° C. for 48 h. A growth curve was made, and it was found that the strain reached a stationary phase after being cultured at 37° C. for 12 h. At the same time, it was observed that the strain performs heterofermentation, and produces acid and gas from glucose.

The *L. mucosae* GDMCC60460 was inoculated into MRS media (containing 0.05% cysteine) and cultured at 10, 15, 20, 25, 30, 35, 40, 45 and 50° C. for 48 h respectively, and the growth conditions were observed. It was found that the strain grows well at 20-35° C. and can still grow at 45° C., but hardly grows at or below 15° C. or at 50° C.

After being inoculated into the MRS medium (containing 0.05% cysteine) and cultured at 37° C. for 48 h, the *L. mucosae* GDMCC60460 was transferred into a fresh MRS medium (containing 0.05% cysteine) and cultured under the same conditions for 30 h. The bacterial cells were centrifuged at 6000 g for 15 min. After being washed with 0.9% normal saline, the bacterial cells were centrifuged again at 6000 g for 10 min. The bacterial cells were resuspended in a 30% sucrose solution, and frozen and stored at −80° C. for later use.

EXAMPLE 1-3

Effect of *L. mucosae* on Body Weight of Influenza Mice 40 healthy ICR female mice weighing 20-24 g were randomly divided into five groups. The five groups were respectively named: a blank control group (Control), an influenza model group (Model), a drug treatment group with administration of ribavirin (Treatment), a *L. mucosae* intervention group with intragastric administration of *L. mucosae* GDMCC60460 (GDMCC60460), and a *L. mucosae* intervention group with intragastric administration of *L. mucosae* F1 (F1), with 8 mice in each group.

Two weeks before the experiment, the *L. mucosae* intervention group (GDMCC60460) was intragastrically administered with a *L. mucosae* GDMCC60460 suspension diluent containing $10^9$ CFU of bacteria every day, the *L. mucosae* F1 intervention group (F1) was intragastrically administered with a *L. mucosae* F1 suspension diluent containing the same amount of bacteria every day, and the other groups (Control, Model, Treatment) were intragastrically administered with 0.2 mL of normal saline every day.

On the first day of the experiment, except for the blank control group (Control), the mice in the other four groups were challenged with influenza virus by nasal drip after mild anesthesia with ether. Intragastric administration was still performed on the day. The *L. mucosae* intervention group (GDMCC60460) was intragastrically administered with a *L. mucosae* GDMCC60460 suspension diluent containing $10^9$ CFU of bacteria, the *L. mucosae* F1 intervention group (F1) was intragastrically administered with a *L. mucosae* F1 suspension diluent containing the same amount of bacteria, and the other groups (Control, Model and Treatment) were intragastrically administered with 0.2 mL of normal saline every day.

On the second day of the experiment, the drug treatment group with administration of ribavirin (Treatment) was injected intraperitoneally with the drug ribavirin for treatment.

Intragastric administration was continued for 4 days after challenge. The *L. mucosae* intervention group (GDMCC60460) was intragastrically administered with a *L. mucosae* GDMCC60460 suspension diluent containing $10^9$ CFU of bacteria, the *L. mucosae* F1 intervention group (F1) was intragastrically administered with a *L. mucosae* F1 suspension diluent containing the same amount of bacteria, and the other groups (Control, Model and Treatment) were intragastrically administered with 0.2 mL of normal saline every day.

During the 5 days of the experiment, the mice were weighed each day before intragastric administration, and the changes in body weight were continuously recorded for five days. The results are shown in FIG. 1.

It can be seen from FIG. 1 that the body weight of mice began to decrease on the third day after challenge, and the weight loss was the most obvious on the fourth day ($P<0.05$). Compared with the control group (Control), the body weight of the model group (Model) decreased by more than 10%, the body weight of the drug treatment group (Treatment) decreased by about 5%, the body weight of the *L. mucosae* F1 intervention group decreased by about 5.5%, and the body weight of the *L. mucosae* GDMCC60460 intervention group decreased by only 3%.

It shows that the *L. mucosae* GDMCC60460 in the disclosure can significantly improve the weight loss symptoms of influenza mice.

EXAMPLE 1-4

Effect of *L. mucosae* on Blood Indexes of Influenza Mice 40 healthy ICR female mice weighing 20-24 g were randomly divided into five groups. The five groups were respectively named: a blank control group (Control), an influenza model group (Model), a drug treatment group with administration of ribavirin (Treatment), a *L. mucosae* intervention group with intragastric administration of *L. mucosae* (GDMCC60460), and a *L. mucosae* intervention group with intragastric administration of *L. mucosae* F1 (F1), with 8 mice in each group.

Two weeks before the experiment, the *L. mucosae* intervention group (GDMCC60460) was intragastrically administered with a *L. mucosae* suspension diluent containing $10^9$ CFU of bacteria every day, the *L. mucosae* F1 intervention group (F1) was intragastrically administered with a *L. mucosae* F1 suspension diluent containing the same amount of bacteria every day, and the other groups (Control, Model, Treatment) were intragastrically administered with 0.2 mL of normal saline every day.

On the first day of the experiment, except the blank control group (Control), the other four groups were challenged with influenza virus by nasal drip after mild anesthesia with ether. Intragastric administration was still performed on the day. The *L. mucosae* intervention group (GDMCC60460) was intragastrically administered with a *L. mucosae* GDMCC60460 suspension diluent containing $10^9$ CFU of bacteria, the *L. mucosae* F1 intervention group (F1) was intragastrically administered with a *L. mucosae* F1 suspension diluent containing the same amount of bacteria, and the other groups (Control, Model and Treatment) were intragastrically administered with 0.2 mL of normal saline every day.

On the second day of the experiment, the drug treatment group with administration of ribavirin (Treatment) was injected intraperitoneally with the drug ribavirin for treatment.

Intragastric administration was continued for 4 days after challenge. The *L. mucosae* intervention group (GDMCC60460) was intragastrically administered with a *L. mucosae* GDMCC60460 suspension diluent containing $10^9$ CFU of bacteria, the *L. mucosae* F1 intervention group (F1) was intragastrically administered with a *L. mucosae* F1 suspension diluent containing the same amount of bacteria, and the other groups (Control, Model and Treatment) were intragastrically administered with 0.2 mL of normal saline every day.

The mice were sacrificed after blood collection on the fifth day after challenge. The collected mouse blood was placed in an anticoagulant tube and shaken gently to make the blood fully contact an anticoagulant. Then the blood was sent to an animal hospital for routine analysis and detection of blood (in the early stage of influenza virus infection, a large number of natural immune cells such as neutrophils and lymphocytes will participate in the defense process, therefore, the routine analysis and detection of blood focuses on detecting changes in the neutrophils and lymphocytes). The results are shown in FIGS. 2-3.

Figure 2:
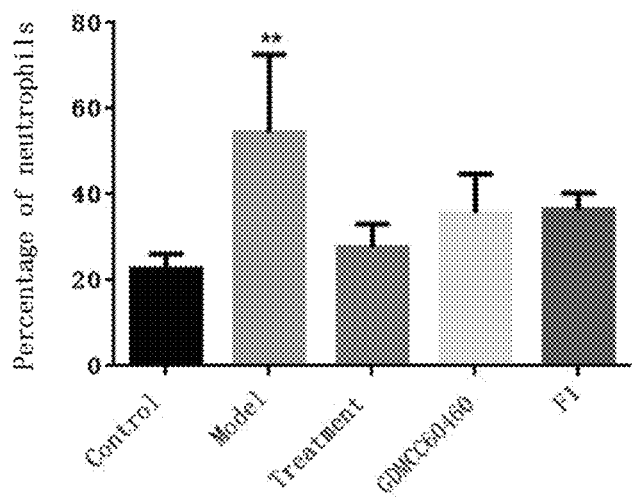
FIG. 2 shows comparison of the blood test index (neutrophils) of different groups of influenza mice (*L. mucosae*).
Figure 3:
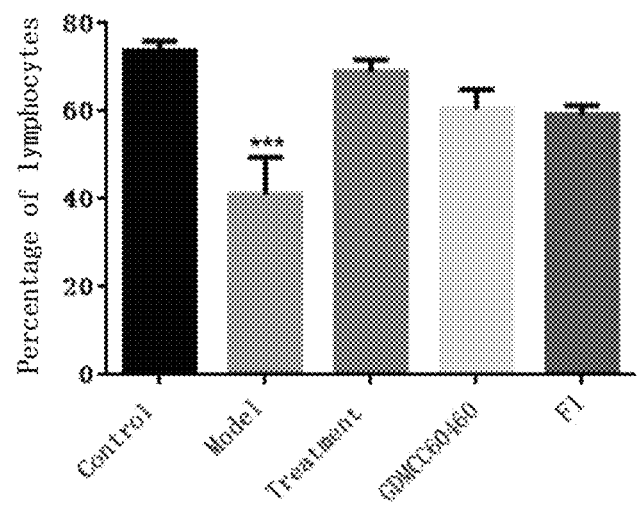
FIG. 3 shows comparison of the blood test index (lymphocytes) of different groups of influenza mice (*L. mucosae*).

As can be seen from FIGS. 2-3, compared with the blank control group (Control), the neutrophils in the model group (Model) significantly increased and the lymphocytes in the model group (Model) significantly decreased, while the other four groups had no significant change.

It is shown that the *L. mucosae* GDMCC60460 in the disclosure can play the same immune regulating function on the body as the ribavirin drug.

EXAMPLE 1-5

Effect of *L. mucosae* on Inflammation of Respiratory Tract Infection in Influenza Mice 40 healthy ICR female mice weighing 20-24 g were randomly divided into five groups. The five groups were respectively named: a blank control group (Control), an influenza model group (Model), a drug treatment group with administration of ribavirin (Treatment), a *L. mucosae* intervention group with intragastric administration of *L. mucosae* (GDMCC60460), and a *L. mucosae* intervention group with intragastric administration of *L. mucosae* F1 (F1), with 8 mice in each group.

Two weeks before the experiment, the *L. mucosae* intervention group (GDMCC60460) was intragastrically administered with a *L. mucosae* GDMCC60460 suspension diluent containing $10^9$ CFU of bacteria every day, the *L. mucosae* F1 intervention group (F1) was intragastrically administered with a *L. mucosae* F1 suspension diluent containing the same amount of bacteria every day, and the other groups (Control, Model, Treatment) were intragastrically administered with 0.2 mL of normal saline every day.

On the first day of the experiment, except the blank control group (Control), the other four groups were challenged with influenza virus by nasal drip after mild anesthesia with ether. Intragastric administration was still performed on the day. The *L. mucosae* intervention group (GDMCC60460) was intragastrically administered with a *L. mucosae* GDMCC60460 suspension diluent containing $10^9$ CFU of bacteria, the *L. mucosae* F1 intervention group (F1) was intragastrically administered with a *L. mucosae* F1 suspension diluent containing the same amount of bacteria, and the other groups (Control, Model and Treatment) were intragastrically administered with 0.2 mL of normal saline every day.

On the second day of the experiment, the drug treatment group with administration of ribavirin (Treatment) was injected intraperitoneally with the drug ribavirin for treatment.

Intragastric administration was continued for 4 days after challenge. The *L. mucosae* intervention group (GDMCC60460) was intragastrically administered with a *L. mucosae* GDMCC60460 suspension diluent containing $10^9$ CFU of bacteria, the *L. mucosae* F1 intervention group (F1) was intragastrically administered with a *L. mucosae* F1 suspension diluent containing the same amount of bacteria, and the blank control group and influenza model group (Control and Model) were intragastrically administered with 0.2 mL of normal saline every day.

The mice were sacrificed after blood collection on the fifth day after challenge. The left lungs of the mice were immediately removed and fixed in 4% paraformaldehyde. The lungs were histopathologically sectioned after fixation. The histopathological sections of the mouse lungs were subjected to hematoxylin-eosin staining after sectioning. The histopathological sections of the mouse lungs were histopathologically scored by professional technicians. The results are shown in FIG. 4.

Figure 4:
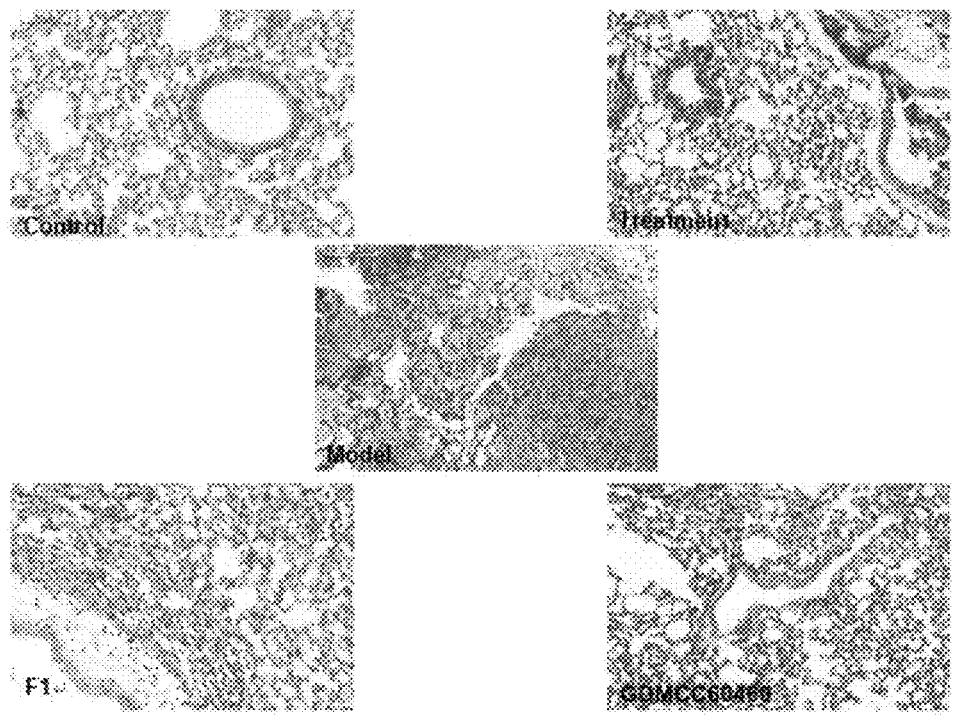
FIG. 4 shows comparison of histopathological sections of lungs of different groups of influenza mice (*L. mucosae*).

It can be seen from FIG. 4 that the lung tissue structures of the mice of the blank control group (Control) are relatively complete, and have no infiltration of inflammatory cells; the mice of the model group (Model) show large-scale characterization of inflammation and even hyperemia; the lungs of the mice of the treatment group (Treatment) and the *L. mucosae* intervention group (GDMCC60460) have mild infiltration of inflammatory cells, which occurs near the bronchus.

The above animal experiments show that influenza infection can cause influenzal pneumonia in mice. After the lungs are infected by the virus, the tissue structure is destroyed and massive inflammatory infiltration occurs. The *L. mucosae* GDMCC60460 of the disclosure can alleviate lung inflammation and pneumonia symptoms in mice, and is equivalent in effect to the ribavirin drug treatment commonly used for influenza.

EXAMPLE 1-6

Effect of *L. mucosae* on Viral Load in Lungs of Influenza Mice 40 healthy ICR female mice weighing 20-24 g were randomly divided into five groups. The five groups were respectively named: a blank control group (Control), an influenza model group (Model), a drug treatment group with administration of ribavirin (Treatment), a *L. mucosae* intervention group with intragastric administration of *L. mucosae* (GDMCC60460), and a *L. mucosae* intervention group with intragastric administration of *L. mucosae* F1 (F1), with 8 mice in each group.

Two weeks before the experiment, the *L. mucosae* intervention group (GDMCC60460) was intragastrically administered with a *L. mucosae* suspension diluent containing $10^9$ CFU of bacteria every day, the *L. mucosae* F1 intervention group (F1) was intragastrically administered with a *L. mucosae* F1 suspension diluent containing the same amount of bacteria every day, and the other groups (Control, Model, Treatment) were intragastrically administered with 0.2 mL of normal saline every day.

On the first day of the experiment, except the blank control group (Control), the other four groups were challenged with influenza virus by nasal drip after mild anesthesia with ether. Intragastric administration was still performed on the day. The *L. mucosae* intervention group (GDMCC60460) was intragastrically administered with a *L. mucosae* GDMCC60460 suspension diluent containing $10^9$ CFU of bacteria, the *L. mucosae* F1 intervention group (F1) was intragastrically administered with a *L. mucosae* F1 suspension diluent containing the same amount of bacteria, and the other groups (Control, Model, Treatment) were intragastrically administered with 0.2 mL of normal saline every day.

Intragastric administration was continued for 4 days after challenge. The *L. mucosae* intervention group (GDMCC60460) was intragastrically administered with a *L. mucosae* GDMCC60460 suspension diluent containing $10^9$ CFU of bacteria, the *L. mucosae* F1 intervention group (F1) was intragastrically administered with a *L. mucosae* F1 suspension diluent containing the same amount of bacteria, and the other groups (Control, Model, Treatment) were intragastrically administered with 0.2 mL of normal saline every day.

The mice were sacrificed after blood collection on the fifth day after challenge. After the mice were sacrificed, the right lung tissues of the mice were taken out and placed in 1 mL of TRIZOL, and cryopreserved in a refrigerator at −80° C. for later use. During extraction, the right lung tissue samples were thawed on ice, and then ground using a DEPC-treated sterile grinder. 200 μL of chloroform was added, the mixture was mixed thoroughly and centrifuged at 4° C. and 12000 rpm for 10 min, and 500 μL of supernatant was removed. An equal volume of isopropanol was added, the mixture was mixed thoroughly and centrifuged at 4° C. and 12000 rpm for 10 min, and the supernatant was removed. 75% ethanol was added for washing RNA once, the mixture was centrifuged at 4° C. and 12000 rpm for 10 min, and the supernatant was removed. After the ethanol evaporated to dryness, 40 μL of DEPC treating water was added to dissolve the RNA. The extracted RNA was cryopreserved in the refrigerator at −80° C. for later use.

A qPCR method was used to determine the viral load, GAPDH was used as the internal reference, a classic $2^{-\Delta\Delta t}$ calculation method was used, and the model group was used as contrast processing data. The results are shown in FIG. 5.

Figure 5:
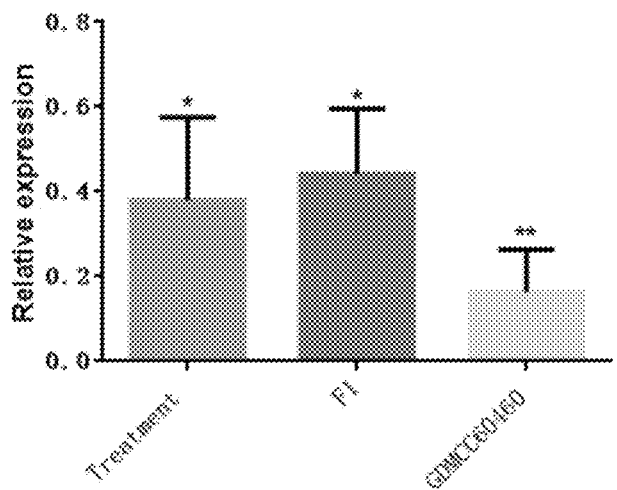
FIG. 5 shows comparison of viral load of lungs of different groups of influenza mice (*L. mucosae*).

It can be seen from FIG. 5 that the viral load in the lungs of mice of the drug treatment group (Treatment) is 38.03% of that of the model group, while the viral load in the lungs of mice of the *L. mucosae* intervention group (GDMCC60460) was only 16.30% of that of the model group.

The above experiments show that the *L. mucosae* GDMCC60460 of the disclosure can significantly reduce the viral load in the lungs of mice infected with influenza, with significant difference (P=0.0022). The reduction in viral load in the lungs of mice of both the *L. mucosae* F1 group and the drug treatment group (Treatment) has significance (P values are 0.0309 and 0.0170, respectively). It is sufficient to show that the therapeutical effect of the *L. mucosae* GDMCC60460 of the disclosure is better than that of influenza drugs in terms of resistance to virus infection.

EXAMPLE 2-1

Screening and Identification of *B. breve*

1. Screening

Human feces was used as a sample. After the sample was pretreated, the sample was stored in about 20% glycerol in a refrigerator at −80° C. After being taken out and thawed, the sample was mixed, and 0.5 mL of the sample was pipetted and added to 4.5 mL. The sample was subjected to gradient dilution with 0.9% normal saline containing 0.05% cysteine. An appropriate gradient diluent was selected and coated on an MRS plate supplemented with 0.05% cysteine, and was cultured at 37° C. for 48 h. Typical colonies were selected and streaked on the MRS plate for purification. Single colonies were selected and transferred to a liquid MRS medium (containing 0.05% cysteine) for enrichment culture. The bacteria were preserved in 30% glycerol to obtain a strain CCFM1026 and a strain B1.

2. Identification

The genomes of the CCFM1026 and the B1 were extracted. The 16S rDNAs of the CCFM1026 and the B1 were subjected to amplification and sequencing (Shanghai Sangon Biotech Co., Ltd.). The sequences were compared in GenBank. The results showed that the Query cover of the strain and *B. breve* is 100% and the identity (Ident) is 99%, so the strains were determined to be *B. breve* and were named as *B. breve* CCFM1026 and *B. breve* B1.

EXAMPLE 2-2

Culture of *B. breve*

The *B. breve* CCFM1026 was inoculated into an MRS solid medium (containing 0.05% cysteine) and cultured at 37° C. for 48 h. The colonies were observed and were found to be round and white.

The bacterial cells were observed and stained under a microscope, and it was found that the bacterial cells are short rod-shaped, are Gram-positive, are irregularly stained with methylene blue staining, have no spores, flagella and capsules, and do not move.

The *B. breve* CCFM1026 was inoculated into an MRS liquid medium (containing 0.05% cysteine) and cultured at 37° C. for 48 h. A growth curve was made, and it was found that the strain reached a stationary phase after being cultured at 37° C. for 30 h. The strain performs atypical heterolactic fermentation using glucose.

After being cultured in the MRS medium (containing 0.05% cysteine) at 37° C. for 48 h, the *B. breve* CCFM1026 was transferred into a fresh MRS medium (containing 0.05% cysteine) and cultured under the same conditions for 30 h. The bacterial cells were centrifuged at 6000 g for 15 min. After being washed with 0.9% normal saline, the bacterial cells were centrifuged again at 6000 g for 10 min. The bacterial cells were resuspended in a 30% sucrose solution, and frozen and stored at −80° C. for later use.

EXAMPLE 2-3

Effect of *B. breve* on Body Weight of Influenza Mice 40 healthy ICR female mice weighing 20-24 g were randomly divided into five groups. The five groups were respectively named: a blank control group (Control), an influenza model group (Model), a drug treatment group with administration of ribavirin (Treatment), a *B. breve* intervention group with intragastric administration of *B. breve* CCFM1026 (CCFM1026), and a *B. breve* intervention group with intragastric administration of *B. breve* B1 (B1), with 8 mice in each group.

Two weeks before the experiment, the *B. breve* intervention group (CCFM1026) was intragastrically administered with a *B. breve* CCFM1026 suspension diluent containing $10^9$ CFU of bacteria, the *B. breve* B1 intervention group (B1) was intragastrically administered with a *B. breve* B1 suspension diluent containing the same amount of bacteria, and the other groups (Control, Model and Treatment) were intragastrically administered with 0.2 mL of normal saline every day.

On the first day of the experiment, except the blank control group (Control), the other four groups were challenged with influenza virus by nasal drip after mild anesthesia with ether. Intragastric administration was still performed on the day. The *B. breve* intervention group (CCFM1026) was intragastrically administered with a *B. breve* CCFM1026 suspension diluent containing $10^9$ CFU of bacteria, the *B. breve* B1 intervention group (B1) was intragastrically administered with a *B. breve* B1 suspension diluent containing the same amount of bacteria, and the other groups (Control, Model and Treatment) were intragastrically administered with 0.2 mL of normal saline every day.

On the second day of the experiment, the drug treatment group with administration of ribavirin (Treatment) was injected intraperitoneally with the drug ribavirin for treatment.

Intragastric administration was continued for 4 days after challenge. The *B. breve* intervention group (CCFM1026) was intragastrically administered with a *B. breve* CCFM1026 suspension diluent containing $10^9$ CFU of bacteria, the *B. breve* B1 intervention group (B1) was intragastrically administered with a *B. breve* B1 suspension diluent containing the same amount of bacteria, and the other groups (Control, Model and Treatment) were intragastrically administered with 0.2 mL of normal saline every day.

During the 5 days of the experiment, the mice were weighed each day before intragastric administration, and the changes in body weight were continuously recorded for five days. The results are shown in FIG. 6.

Figure 6:
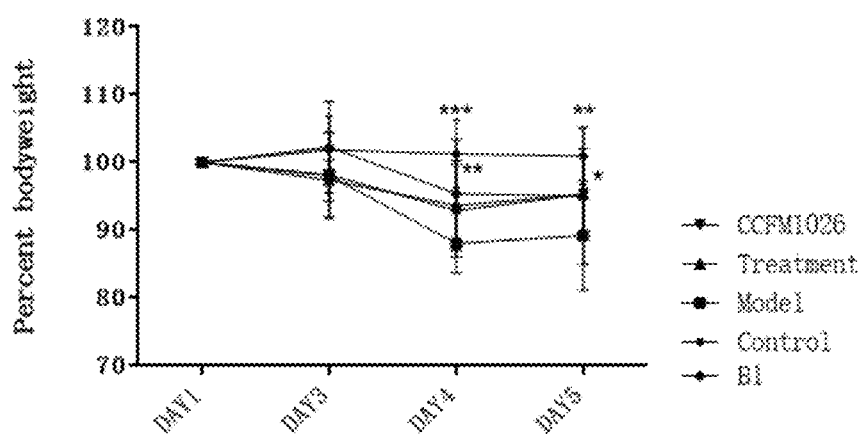
FIG. 6 shows comparison of body weight changes of different groups of influenza mice (*B. breve*).

It can be seen from FIG. 6 that the body weight of mice began to decrease on the third day after challenge, and the weight loss was the most obvious on the fourth day (P<0.05). Compared with the control group (Control), the body weight of the model group (Model) decreased by more than 10%, the body weight of the drug treatment group (Treatment) decreased by about 5%, while the body weight of the *B. breve* intervention group (CCFM1026) and the *B. breve* B1 group decreased by only 5%.

It shows that the *B. breve* CCFM1026 and B1 in the disclosure can significantly improve the weight loss symptoms of influenza mice.

EXAMPLE 2-4

Effect of *B. breve* on Blood Indexes of Influenza Mice 40 healthy ICR female mice weighing 20-24 g were randomly divided into five groups. The five groups were respectively named: a blank control group (Control), an influenza model group (Model), a drug treatment group with administration of ribavirin (Treatment), a *B. breve* intervention group with intragastric administration of *B. breve* CCFM1026 (CCFM1026), and a *B. breve* intervention group with intragastric administration of *B. breve* B1 (B1), with 8 mice in each group.

Two weeks before the experiment, the *B. breve* CCFM1206 intervention group (CCFM1206) was intragastrically administered with a *B. breve* CCFM1206 suspension diluent containing $10^9$ CFU of bacteria, the *B. breve* B1 intervention group (B1) was intragastrically administered with a *B. breve* B1 suspension diluent containing the same amount of bacteria, and the other groups (Control, Model and Treatment) were intragastrically administered with 0.2 mL of normal saline every day.

On the first day of the experiment, except the blank control group (Control), the other four groups were challenged with influenza virus by nasal drip after mild anesthesia with ether. Intragastric administration was still performed on the day. The *B. breve* intervention group (CCFM1026) was intragastrically administered with a *B. breve* CCFM1026 suspension diluent containing $10^9$ CFU of bacteria, the *B. breve* B1 intervention group (B1) was intragastrically administered with a *B. breve* B1 suspension diluent containing the same amount of bacteria, and the other groups (Control, Model and Treatment) were intragastrically administered with 0.2 mL of normal saline every day.

On the second day of the experiment, the drug treatment group with administration of ribavirin (Treatment) was injected intraperitoneally with the drug ribavirin for treatment.

Intragastric administration was continued for 4 days after challenge. The *B. breve* intervention group (CCFM1026) was intragastrically administered with a *B. breve* CCFM1026 suspension diluent containing $10^9$ CFU of bacteria, the *B. breve* B1 intervention group (B1) was intragastrically administered with a *B. breve* B1 suspension diluent containing the same amount of bacteria, and the other groups (Control, Model and Treatment) were intragastrically administered with 0.2 mL of normal saline every day.

The mice were sacrificed after blood collection on the fifth day after challenge. The collected mouse blood was placed in an anticoagulant tube and shaken gently to make the blood fully contact an anticoagulant. Then the blood was sent to an animal hospital for routine analysis and detection of blood (in the early stage of influenza virus infection, a large number of natural immune cells such as neutrophils and lymphocytes will participate in the defense process, therefore, the routine analysis and detection of blood focuses on detecting changes in the neutrophils and lymphocytes). The results are shown in FIGS. 7-8.

Figure 7:
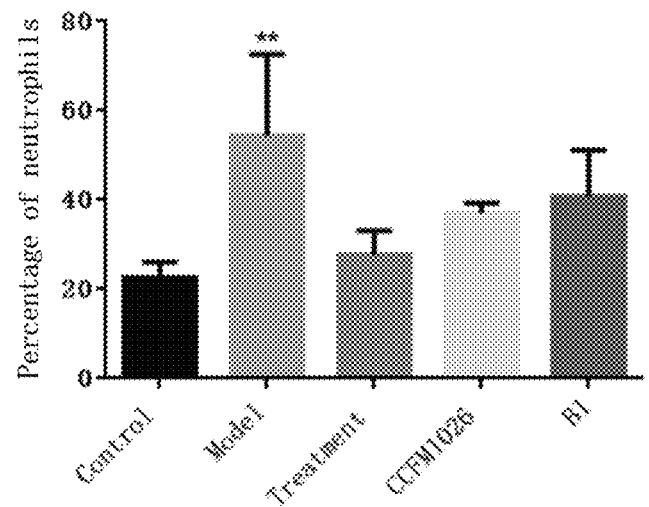
FIG. 7 shows comparison of the blood test index (neutrophils) of different groups of influenza mice (*B. breve*).
Figure 8:
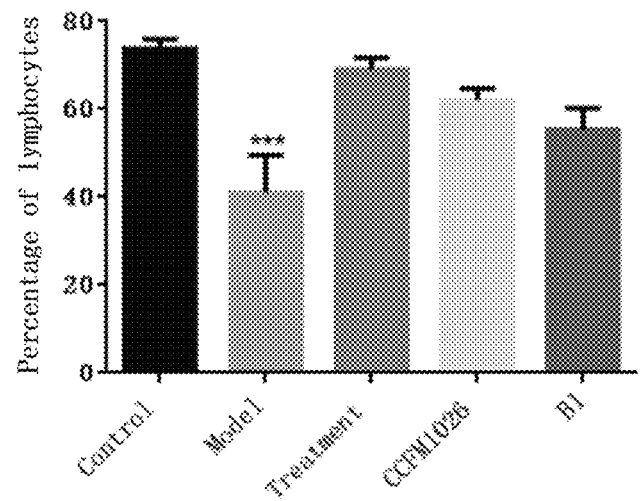
FIG. 8 shows comparison of the blood test index (lymphocytes) of different groups of influenza mice (*B. breve*).

As can be seen from FIGS. 7-8, compared with the blank control group (Control), the percentages of neutrophils and lymphocytes in mice of the model group (Model) were significantly abnormal, and were significantly different from those of the control group (control) (p values are 0.0015 and 0.0011, respectively). Yet, the percentages of neutrophils and lymphocytes in mice of the *B. breve* intervention group (CCFM1026) and the drug treatment group (Treatment) tended to those of the blank control group (Control) without significant differences.

It is shown that the *B. breve* of the disclosure has the same effect as the ribavirin drug, and can actively participate in the influenza-related immune regulation of mice and alleviate the symptoms of influenza in mice.

EXAMPLE 2-5

Effect of *B. breve* on Inflammation of Respiratory Tract Infection in Influenza Mice 40 healthy ICR female mice weighing 20-24 g were randomly divided into five groups. The five groups were respectively named: a blank control group (Control), an influenza model group (Model), a drug treatment group with administration of ribavirin (Treatment), a *B. breve* intervention group with intragastric administration of *B. breve* CCFM1026 (CCFM1026), and a *B. breve* intervention group with intragastric administration of *B. breve* B1 (B1), with 8 mice in each group.

Two weeks before the experiment, the *B. breve* CCFM1206 intervention group (CCFM1206) was intragastrically administered with a *B. breve* CCFM1206 suspension diluent containing $10^9$ CFU of bacteria, the *B. breve* B1 intervention group (B1) was intragastrically administered with a *B. breve* B1 suspension diluent containing the same amount of bacteria, and the other groups (Control, Model and Treatment) were intragastrically administered with 0.2 mL of normal saline every day.

On the first day of the experiment, except the blank control group (Control), the other four groups were challenged with influenza virus by nasal drip after mild anesthesia with ether. Intragastric administration was still performed on the day. The *B. breve* intervention group (CCFM1026) was intragastrically administered with a *B. breve* CCFM1026 suspension diluent containing $10^9$ CFU of bacteria, the *B. breve* B1 intervention group (B1) was intragastrically administered with a *B. breve* B1 suspension diluent containing the same amount of bacteria, and the other groups (Control, Model and Treatment) were intragastrically administered with 0.2 mL of normal saline every day.

On the second day of the experiment, the drug treatment group with administration of ribavirin (Treatment) was injected intraperitoneally with the drug ribavirin for treatment.

Intragastric administration was continued for 4 days after challenge. The *B. breve* intervention group (CCFM1026) was intragastrically administered with a *B. breve* CCFM1026 suspension diluent containing $10^9$ CFU of bacteria, the *B. breve* B1 intervention group (B1) was intragastrically administered with a *B. breve* B1 suspension diluent containing the same amount of bacteria, and the other groups (Control, Model and Treatment) were intragastrically administered with 0.2 mL of normal saline every day.

The mice were sacrificed after blood collection on the fifth day after challenge. The left lungs of the mice were immediately removed and fixed in 4% paraformaldehyde. The lungs were histopathologically sectioned after fixation. The histopathological sections of the mouse lungs were subjected to hematoxylin-eosin staining after sectioning. The histopathological sections of the mouse lungs were histopathologically scored by professional technicians. The results are shown in FIG. 9.

Figure 9:
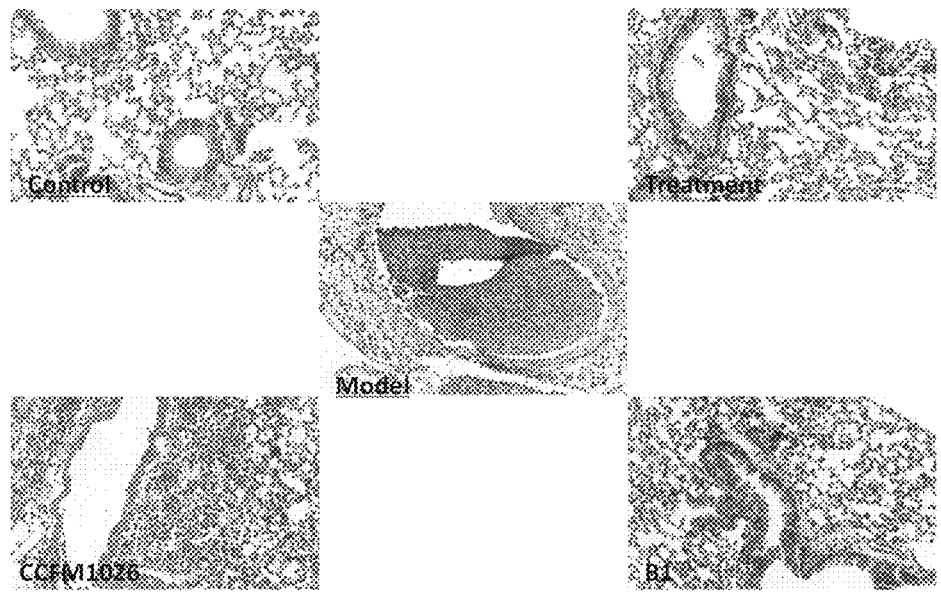
FIG. 9 shows comparison of histopathological sections of lungs of different groups of influenza mice (*B. breve*).

It can be seen from FIG. 9 that the lung tissue structures of the mice of the blank control group (Control) are relatively complete, and have no infiltration of inflammatory cells; the mice of the model group (Model) have severe inflammatory infiltration, and even local hemorrhage; the *B. breve* B1 intervention group (B1) showed moderate inflammatory infiltration near the bronchus; while the treatment group (Treatment) and the *B. breve* intervention group (CCFM1026) had relatively mild inflammation in the lungs of mice.

The above animal experiments show that influenza infection can cause influenzal pneumonia in mice. After the lungs are infected by the virus, the tissue structure is destroyed and massive inflammatory infiltration occurs. The *B. breve* of the disclosure can alleviate lung inflammation and pneumonia symptoms in mice, and is equivalent in effect to the ribavirin drug treatment commonly used for influenza.

EXAMPLE 2-6

Effect of *B. breve* on Viral Load in Lungs of Influenza Mice 40 healthy ICR female mice weighing 20-24 g were randomly divided into five groups. The five groups were respectively named: a blank control group (Control), an influenza model group (Model), a drug treatment group with administration of ribavirin (Treatment), a *B. breve* intervention group with intragastric administration of *B. breve* CCFM1026 (CCFM1026), and a *B. breve* intervention group with intragastric administration of *B. breve* B1 (B1), with 8 mice in each group.

Two weeks before the experiment, the *B. breve* CCFM1206 intervention group (CCFM1206) was intragastrically administered with a *B. breve* CCFM1206 suspension diluent containing $10^9$ CFU of bacteria, the *B. breve* B1 intervention group (B1) was intragastrically administered with a *B. breve* B1 suspension diluent containing the same amount of bacteria, and the other groups (Control, Model and Treatment) were intragastrically administered with 0.2 mL of normal saline every day.

On the first day of the experiment, except the blank control group (Control), the other four groups were challenged with influenza virus by nasal drip after mild anesthesia with ether. Intragastric administration was still performed on the day. The *B. breve* intervention group (CCFM1026) was intragastrically administered with a *B. breve* CCFM1026 suspension diluent containing $10^9$ CFU of bacteria, the *B. breve* B1 intervention group (B1) was intragastrically administered with a *B. breve* B1 suspension diluent containing the same amount of bacteria, and the other groups (Control, Model and Treatment) were intragastrically administered with 0.2 mL of normal saline every day.

On the second day of the experiment, the drug treatment group with administration of ribavirin (Treatment) was injected intraperitoneally with the drug ribavirin for treatment.

Intragastric administration was continued for 4 days after challenge. The *B. breve* intervention group (CCFM1026) was intragastrically administered with a *B. breve* CCFM1026 suspension diluent containing $10^9$ CFU of bacteria, the *B. breve* B1 intervention group (B1) was intragastrically administered with a *B. breve* B1 suspension diluent containing the same amount of bacteria, and the other groups (Control, Model and Treatment) were intragastrically administered with 0.2 mL of normal saline every day.

The mice were sacrificed after blood collection on the fifth day after challenge. After the mice were sacrificed, the right lung tissues of the mice were taken out and placed in 1 mL of TRIZOL, and cryopreserved in a refrigerator at −80° C. for later use. During extraction, the right lung tissue samples were thawed on ice, and then ground using a DEPC-treated sterile grinder. 200 µL of chloroform was added, the mixture was mixed thoroughly and centrifuged at 4° C. and 12000 rpm for 10 min, and 500 µL of supernatant was removed. An equal volume of isopropanol was added, the mixture was mixed thoroughly and centrifuged at 4° C. and 12000 rpm for 10 min, and the supernatant was removed. 75% ethanol was added for washing RNA once, the mixture was centrifuged at 4° C. and 12000 rpm for 10 min, and the supernatant was removed. After the ethanol evaporated to dryness, 40 µL of DEPC treating water was added to dissolve the RNA. The extracted RNA was cryopreserved in the refrigerator at −80° C. for later use.

A qPCR method was used to determine the relative expression quantity of MxA (the body will react defensively to the influenza virus to clear the invading virus and restore health, MxA is an antiviral protein secreted by the body, which can effectively prevent the virus from replicating), GAPDH was used as the internal reference, a classic $2^{-\Delta\Delta t}$ calculation method was used, and the model group was used as the contrast processing data. The results are shown in FIG. 10.

Figure 10:
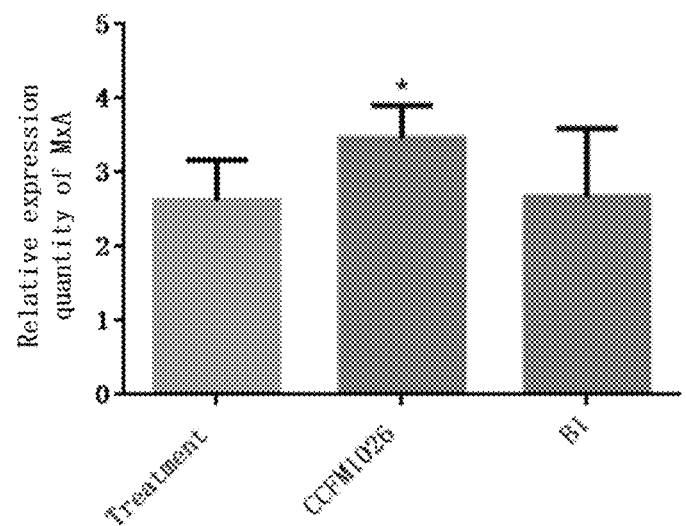
FIG. 10 shows comparison of expression quantity of antiviral protein MxA in lungs of different groups of influenza mice (*B. breve*).

It can be seen from FIG. 10 that the expression quantity of MxA in the lungs of mice of the drug treatment group (Treatment) is 2.62 times that of the model group (Model), and the expression quantity of MxA in the lungs of mice of the *B. breve* B1 intervention group is 2.67 times that of the model group (Model), with no significant difference. Yet, the expression quantity of MxA in the lungs of mice of the *B. breve* intervention group (CCFM1026) is 3.46 times that of the model group (Model), which is significantly improved (p value is 0.0292).

The above experiments show that the *B. breve* CCFM1026 of the disclosure can significantly enhance the immunity ability of influenza mice, and promote increase of the expression quantity of MxA antiviral protein, thereby counteracting virus replication, and helping the body to recover. The *B. breve* CCFM1026 significantly alleviates the respiratory tract inflammation, and has even better effect than drug treatment.

EXAMPLE 3-1

Effect of Mixed Bacteria on Body Weight of Influenza Mice 48 healthy ICR female mice weighing 20-24 g were randomly divided into six groups. The six groups were respectively named: a blank control group (Control), an influenza model group (Model), a drug treatment group with administration of ribavirin (Treatment), a *L. mucosae* intervention group with intragastric administration of *L. mucosae* GDMCC60460 (GDMCC60460), a *B. breve* intervention group with intragastric administration of *B. breve* CCFM1026 (CCFM1026), and a bacterial preparation intervention group with intragastric administration of a probiotic mixed preparation (GDMCC60460+1026), with 8 mice in each group.

Two weeks before the experiment, the *L. mucosae* intervention group (GDMCC60460) was intragastrically administered with a *L. mucosae* GDMCC60460 suspension diluent containing $10^9$ CFU of bacteria, the *B. breve* CCFM1206 intervention group (CCFM1206) was intragastrically administered with a *B. breve* CCFM1206 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains $5\times10^8$ CFU bacterial amount of *L. mucosae* GDMCC60460 and $5\times10^8$ CFU bacterial amount of *B. breve* CCFM1026), and the other groups (Control, Model and Treatment) were intragastrically administered with 0.2 mL of normal saline every day.

On the first day of the experiment, except the blank control group (Control), the other five groups were challenged with influenza virus by nasal drip after mild anesthesia with ether. Intragastric administration was still performed on the day. The *L. mucosae* intervention group (GDMCC60460) was intragastrically administered with a *L. mucosae* GDMCC60460 suspension diluent containing $10^9$ CFU of bacteria, the *B. breve* CCFM1026 intervention group (CCFM1026) was intragastrically administered with a *B. breve* CCFM1026 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains $5\times10^8$ CFU bacterial amount of *L. mucosae* GDMCC60460 and $5\times10^8$ CFU bacterial amount of *B. breve* CCFM1026), and the other groups (Control, Model and Treatment) were intragastrically administered with 0.2 mL of normal saline every day.

On the second day of the experiment, the drug treatment group with administration of ribavirin (Treatment) was injected intraperitoneally with the drug ribavirin for treatment.

Intragastric administration was continued for 4 days after challenge. The *L. mucosae* intervention group (GDMCC60460) was intragastrically administered with a *L. mucosae* GDMCC60460 suspension diluent containing $10^9$ CFU of bacteria, the *B. breve* CCFM1026 intervention group (CCFM1026) was intragastrically administered with a *B. breve* CCFM1026 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains $5\times10^8$ CFU bacterial amount of *L. mucosae* GDMCC60460 and $5\times10^8$ CFU bacterial amount of *B. breve* CCFM1026), and the other groups (Control, Model and Treatment) were intragastrically administered with 0.2 mL of normal saline every day.

During the 5 days of the experiment, the mice were weighed each day before intragastric administration, and the changes in body weight were continuously recorded for five days. The results are shown in FIG. 11.

Figure 11:
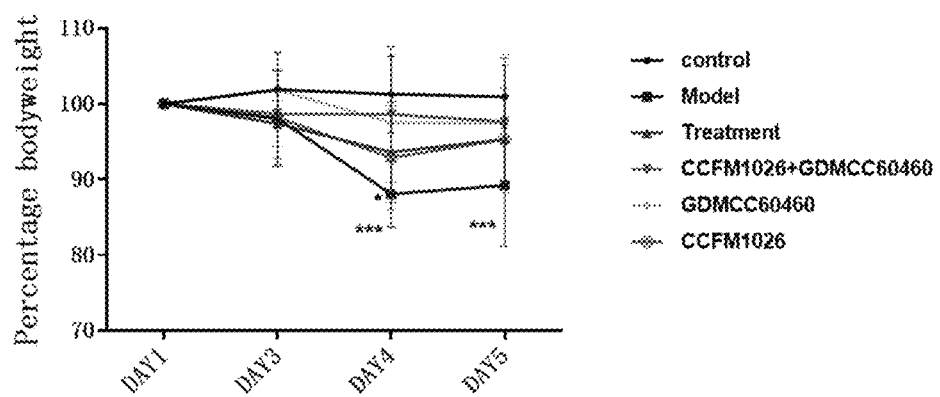
FIG. 11 shows comparison of body weight changes of different groups of influenza mice (mixed bacteria).

It can be seen from FIG. 11 that the body weight of mice began to decrease on the third day after challenge, and the weight loss was the most obvious on the fourth day ($P<0.05$). Compared with the control group (Control), the body weight of the model group (Model) decreased by more than 10%, the body weight of the drug treatment group (Treatment) decreased by about 5%, the body weight of the *L. mucosae* intervention group (GDMCC60460) decreased by about 3%, the body weight of the *B. breve* intervention group (CCFM1026) decreased by about 5%, and the bacterial preparation intervention group (GDMCC60460+1026) mice had the smallest weight loss of less than 3%, and had better intervention effect than those of the drug treatment group (Treatment), the *L. mucosae* intervention group (GDMCC60460), and the *B. breve* intervention group (CCFM1026). It is sufficient to explain that ingestion of the probiotic mixed preparation of the disclosure can obviously alleviate weight loss of influenza mice caused by influenza cold.

EXAMPLE 3-2

Effect of Mixed Bacteria on Blood Indexes of Influenza Mice 48 healthy ICR female mice weighing 20-24 g were randomly divided into six groups. The six groups were respectively named: a blank control group (Control), an influenza model group (Model), a drug treatment group with administration of ribavirin (Treatment), a *L. mucosae* intervention group with intragastric administration of *L. mucosae* GDMCC60460 (GDMCC60460), a *B. breve* intervention group with intragastric administration of *B. breve* CCFM1026 (CCFM1026), and a bacterial preparation intervention group with intragastric administration of a probiotic mixed preparation (GDMCC60460+1026), with 8 mice in each group.

Two weeks before the experiment, the *L. mucosae* intervention group (GDMCC60460) was intragastrically administered with a *L. mucosae* GDMCC60460 suspension diluent containing $10^9$ CFU of bacteria, the *B. breve* CCFM1206 intervention group (CCFM1206) was intragastrically administered with a *B. breve* CCFM1206 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains $5\times10^8$ CFU bacterial amount of *L. mucosae* GDMCC60460 and $5\times10^8$ CFU bacterial amount of *B. breve* CCFM1026), and the other groups (Control, Model and Treatment) were intragastrically administered with 0.2 mL of normal saline every day.

On the first day of the experiment, except the blank control group (Control), the other five groups were challenged with influenza virus by nasal drip after mild anesthesia with ether. Intragastric administration was still performed on the day. The *L. mucosae* intervention group (GDMCC60460) was intragastrically administered with a *L. mucosae* GDMCC60460 suspension diluent containing $10^9$ CFU of bacteria, the *B. breve* CCFM1026 intervention group (CCFM1026) was intragastrically administered with a *B. breve* CCFM1026 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains $5\times10^8$ CFU bacterial amount of *L. mucosae* GDMCC60460 and $5\times10^8$ CFU bacterial amount of *B. breve* CCFM1026), and the other groups (Control, Model and Treatment) were intragastrically administered with 0.2 mL of normal saline every day.

On the second day of the experiment, the drug treatment group with administration of ribavirin (Treatment) was injected intraperitoneally with the drug ribavirin for treatment.

Intragastric administration was continued for 4 days after challenge. The *L. mucosae* intervention group (GDMCC60460) was intragastrically administered with a *L. mucosae* GDMCC60460 suspension diluent containing $10^9$ CFU of bacteria, the *B. breve* CCFM1026 intervention group (CCFM1026) was intragastrically administered with a *B. breve* CCFM1026 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains $5\times10^8$ CFU bacterial amount of *L. mucosae* GDMCC60460 and $5\times10^8$ CFU bacterial amount of *B. breve* CCFM1026), and the other groups (Control, Model and Treatment) were intragastrically administered with 0.2 mL of normal saline every day.

The mice were sacrificed after blood collection on the fifth day after challenge. The collected mouse blood was placed in an anticoagulant tube and shaken gently to make the blood fully contact an anticoagulant. Then the blood was sent to an animal hospital for routine analysis and detection of blood (in the early stage of influenza virus infection, a large number of natural immune cells such as neutrophils and lymphocytes will participate in the defense process, therefore, the routine analysis and detection of blood focuses on detecting changes in the neutrophils and lymphocytes). The results are shown in FIGS. 12-13.

Figure 12:
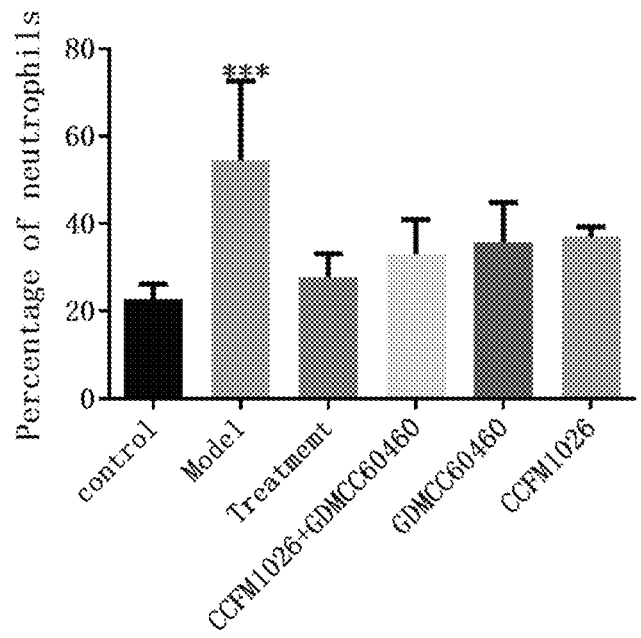
FIG. 12 shows comparison of the blood test index (neutrophils) of different groups of influenza mice (mixed bacteria).
Figure 13:
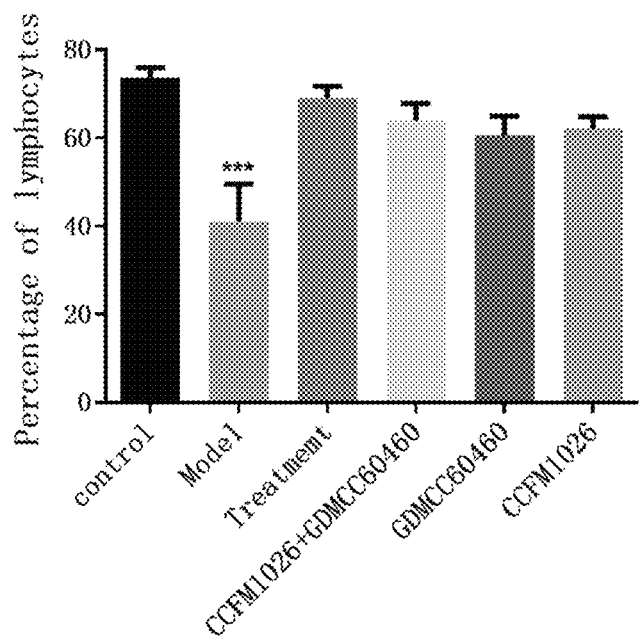
FIG. 13 shows comparison of the blood test index (lymphocytes) of different groups of influenza mice (mixed bacteria).

As can be seen from FIGS. 12-13, after the mice have caught influenza cold, the proportion of natural immune cells in the mice will change differently. That is, the levels of the immune cells such as neutrophils and lymphocytes in the mice of the model group (Model) show changes in different trends, and are significantly different from those in the blank control group (Control). Yet, the indexes of the mice in the intervention group ingesting probiotics tend to normal values and have no significant difference from those of the blank control group (Control). Compared with the model group, in the groups ingesting probiotics, the percentage of neutrophils decreased (Control: 22.60%, GDMCC60460+1026: 33.10%, GDMCC60460: 35.75%, CCFM1026: 37.10%), and correspondingly, the percentage of lymphocytes increased (Control: 73.70%, GDMCC60460+1026: 63.95%, GDMCC60460: 60.56%, CCFM1026: 62.10%). It can be seen that the probiotic mixed preparation group (GDMCC60460+1026) tends to the blank control group (Control) to a slightly stronger extent than the two single-bacterium (GDMCC60460 and CCFM1026) groups. It shows that the probiotics ingested by the mice can participate in the immune regulation of the body, help the body to resist the invasion of influenza virus, and maintain the health of the body, and the effect of the mixed bacterial preparation is better than that of the single bacterium.

EXAMPLE 3-3

Effect of Mixed Bacteria on Inflammation of Respiratory Tract Infection in Influenza Mice 48 healthy ICR female mice weighing 20-24 g were randomly divided into six groups. The six groups were respectively named: a blank control group (Control), an influenza model group (Model), a drug treatment group with administration of ribavirin (Treatment), a *L. mucosae* intervention group with intragastric administration of *L. mucosae* GDMCC60460 (GDMCC60460), a *B. breve* intervention group with intragastric administration of *B. breve* CCFM1026 (CCFM1026), and a bacterial preparation intervention group with intragastric administration of a probiotic mixed preparation (GDMCC60460+1026), with 8 mice in each group.

Two weeks before the experiment, the *L. mucosae* intervention group (GDMCC60460) was intragastrically administered with a *L. mucosae* GDMCC60460 suspension diluent containing $10^9$ CFU of bacteria, the *B. breve* CCFM1206 intervention group (CCFM1206) was intragastrically administered with a *B. breve* CCFM1206 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains $5\times10^8$ CFU bacterial amount of *L. mucosae* GDMCC60460 and $5\times10^8$ CFU bacterial amount of *B. breve* CCFM1026), and the other groups (Control, Model and Treatment) were intragastrically administered with 0.2 mL of normal saline every day.

On the first day of the experiment, except the blank control group (Control), the other five groups were challenged with influenza virus by nasal drip after mild anesthesia with ether. Intragastric administration was still performed on the day. The *L. mucosae* intervention group (GDMCC60460) was intragastrically administered with a *L. mucosae* GDMCC60460 suspension diluent containing $10^9$ CFU of bacteria, the *B. breve* CCFM1026 intervention group (CCFM1026) was intragastrically administered with a *B. breve* CCFM1026 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains $5\times10^8$ CFU bacterial amount of *L. mucosae* GDMCC60460 and $5\times10^8$ CFU bacterial amount of *B. breve* CCFM1026), and the other groups (Control, Model and Treatment) were intragastrically administered with 0.2 mL of normal saline every day.

On the second day of the experiment, the drug treatment group with administration of ribavirin (Treatment) was injected intraperitoneally with the drug ribavirin for treatment.

Intragastric administration was continued for 4 days after challenge. The *L. mucosae* intervention group (GDMCC60460) was intragastrically administered with a *L. mucosae* GDMCC60460 suspension diluent containing $10^9$ CFU of bacteria, the *B. breve* CCFM1026 intervention group (CCFM1026) was intragastrically administered with a *B. breve* CCFM1026 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains 5×10⁸ CFU bacterial amount of *L. mucosae* GDMCC60460 and 5×10⁸ CFU bacterial amount of *B. breve* CCFM1026), and the other groups (Control, Model and Treatment) were intragastrically administered with 0.2 mL of normal saline every day.

The mice were sacrificed after blood collection on the fifth day after challenge. The left lungs of the mice were immediately removed and fixed in 4% paraformaldehyde. The lungs were histopathologically sectioned after fixation. The histopathological sections of the mouse lungs were subjected to hematoxylin-eosin staining after sectioning. The histopathological sections of the mouse lungs were histopathologically scored by professional technicians. The results are shown in FIG. 14.

Figure 14:
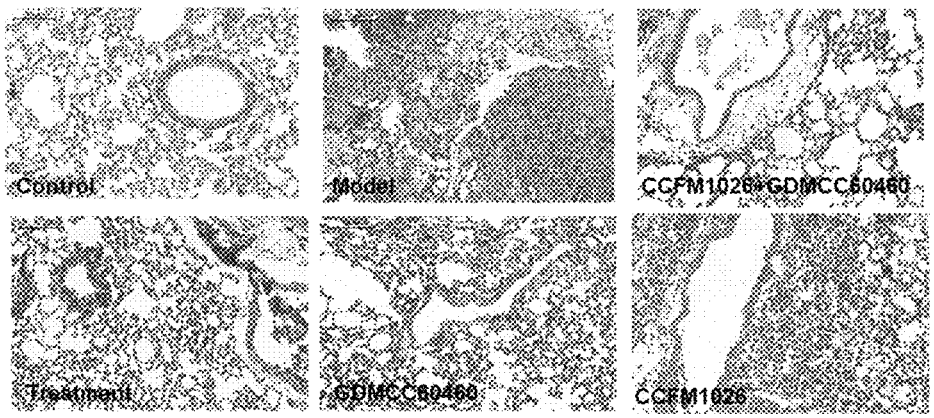
FIG. 14 shows comparison of histopathological sections of lungs of different groups of influenza mice (mixed bacteria).

It can be seen from FIG. 14 that the lung tissue structures of the mice of the blank control group (Control) are relatively complete, and have no infiltration of inflammatory cells; the mice of the model group (Model) show large-scale characterization of inflammation and even hyperemia; and some moderate and mild inflammation can be observed in the lungs of the mice of the treatment group (Treatment) and the probiotic mixed preparation intervention group (GDMCC60460+1026), but the bronchus and other structures are still complete, and the degree of pathology has been relieved to certain extent. Compared with the two single bacterial intervention groups, the mixed bacterial preparation intervention group (GDMCC60460+1026) has better villous integrity of the bronchus and less peripheral inflammation. Although the histopathological scores of the groups are similar, it can still be explained that the mixed bacterial preparation intervention group (GDMCC60460+1026) can reduce the degree of respiratory tract infection in influenza-infected mice to a certain extent, and the effect of the mixed bacterial preparation is better than that of a single bacterium.

EXAMPLE 3-4

Effect of Mixed Bacteria on Viral Load in Lungs of Influenza Mice 48 healthy ICR female mice weighing 20-24 g were randomly divided into six groups. The six groups were respectively named: a blank control group (Control), an influenza model group (Model), a drug treatment group with administration of ribavirin (Treatment), a *L. mucosae* intervention group with intragastric administration of *L. mucosae* GDMCC60460 (GDMCC60460), a *B. breve* intervention group with intragastric administration of *B. breve* CCFM1026 (CCFM1026), and a bacterial preparation intervention group with intragastric administration of a probiotic mixed preparation (GDMCC60460+1026), with 8 mice in each group.

Two weeks before the experiment, the *L. mucosae* intervention group (GDMCC60460) was intragastrically administered with a *L. mucosae* GDMCC60460 suspension diluent containing $10^9$ CFU of bacteria, the *B. breve* CCFM1206 intervention group (CCFM1206) was intragastrically administered with a *B. breve* CCFM1206 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains 5×10⁸ CFU bacterial amount of *L. mucosae* GDMCC60460 and 5×10⁸ CFU bacterial amount of *B. breve* CCFM1026), and the other groups (Control, Model and Treatment) were intragastrically administered with 0.2 mL of normal saline every day.

On the first day of the experiment, except the blank control group (Control), the other five groups were challenged with influenza virus by nasal drip after mild anesthesia with ether. Intragastric administration was still performed on the day. The *L. mucosae* intervention group (GDMCC60460) was intragastrically administered with a *L. mucosae* GDMCC60460 suspension diluent containing $10^9$ CFU of bacteria, the *B. breve* CCFM1026 intervention group (CCFM1026) was intragastrically administered with a *B. breve* CCFM1026 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains 5×10⁸ CFU bacterial amount of *L. mucosae* GDMCC60460 and 5×10⁸ CFU bacterial amount of *B. breve* CCFM1026), and the other groups (Control, Model and Treatment) were intragastrically administered with 0.2 mL of normal saline every day.

On the second day of the experiment, the drug treatment group with administration of ribavirin (Treatment) was injected intraperitoneally with the drug ribavirin for treatment.

Intragastric administration was continued for 4 days after challenge. The *L. mucosae* intervention group (GDMCC60460) was intragastrically administered with a *L. mucosae* GDMCC60460 suspension diluent containing $10^9$ CFU of bacteria, the *B. breve* CCFM1026 intervention group (CCFM1026) was intragastrically administered with a *B. breve* CCFM1026 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains 5×10⁸ CFU bacterial amount of *L. mucosae* GDMCC60460 and 5×10⁸ CFU bacterial amount of *B. breve* CCFM1026), and the other groups (Control, Model and Treatment) were intragastrically administered with 0.2 mL of normal saline every day.

The mice were sacrificed after blood collection on the fifth day after challenge. After the mice were sacrificed, the right lung tissues of the mice were taken out and placed in 1 mL of TRIZOL, and cryopreserved in a refrigerator at −80° C. for later use. During extraction, the right lung tissue samples were thawed on ice, and then ground using a DEPC-treated sterile grinder. 200 µL of chloroform was added, the mixture was mixed thoroughly and centrifuged at 4° C. and 12000 rpm for 10 min, and 500 µL of supernatant was removed. An equal volume of isopropanol was added, the mixture was mixed thoroughly and centrifuged at 4° C. and 12000 rpm for 10 min, and the supernatant was removed. 75% ethanol was added for washing RNA once, the mixture was centrifuged at 4° C. and 12000 rpm for 10 min, and the supernatant was removed. After the ethanol evaporated to dryness, 40 µL of DEPC treating water was added to dissolve the RNA. The extracted RNA was cryopreserved in the refrigerator at −80° C. for later use.

A qPCR method was used to determine the viral load, GAPDH was used as the internal reference, a classic $2^{-\Delta\Delta t}$ calculation method was used, and the model group was used as the contrast processing data. The results are shown in FIG. 15.

Figure 15:
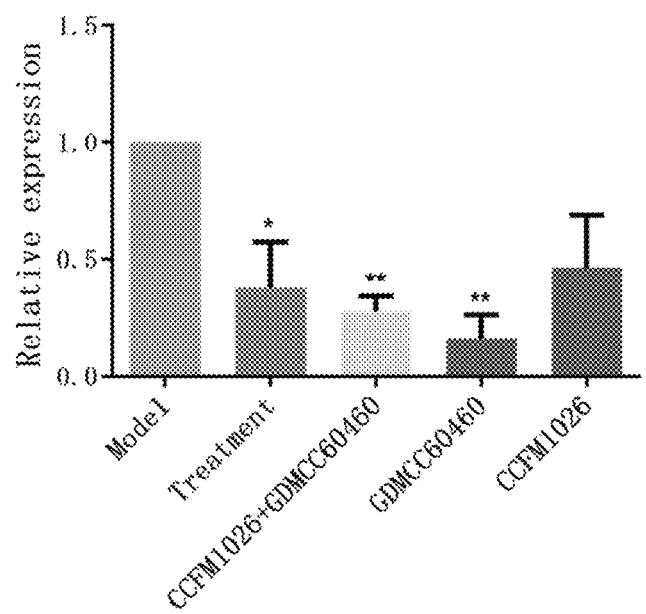
FIG. 15 shows comparison of viral load of lungs of different groups of influenza mice (mixed bacteria).

It can be seen from FIG. 15 that the viral load in the lungs of mice of the intervention groups ingesting probiotics decreased, all being less than 50%. The mixed bacterial preparation intervention group (GDMCC60460+1026) and the *L. mucosae* intervention group significantly decreased, with the p values being 0.0097 and 0.0032 respectively, and average values being 27.68% and 16.3% respectively. The average value of the relative viral load of the drug treatment group was 38.03%. The data shows that the probiotic mixed preparation can significantly reduce the viral load in the lungs of mice infected with influenza, and has better effect than drug treatment.

EXAMPLE 3-5

Effect of Mixed Bacteria on Viral Load in Lungs of Influenza Mice 48 healthy ICR female mice weighing 20-24 g were randomly divided into six groups. The six groups were respectively named: a blank control group (Control), an influenza model group (Model), a drug treatment group with administration of ribavirin (Treatment), a *L. mucosae* intervention group with intragastric administration of *L. mucosae* GDMCC60460 (GDMCC60460), a *B. breve* intervention group with intragastric administration of *B. breve* CCFM1026 (CCFM1026), and a bacterial preparation intervention group with intragastric administration of a probiotic mixed preparation (GDMCC60460+1026), with 8 mice in each group.

Two weeks before the experiment, the *L. mucosae* intervention group (GDMCC60460) was intragastrically administered with a *L. mucosae* GDMCC60460 suspension diluent containing $10^9$ CFU of bacteria, the *B. breve* CCFM1206 intervention group (CCFM1206) was intragastrically administered with a *B. breve* CCFM1206 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains $5\times10^8$ CFU bacterial amount of *L. mucosae* GDMCC60460 and $5\times10^8$ CFU bacterial amount of *B. breve* CCFM1026), and the other groups (Control, Model and Treatment) were intragastrically administered with 0.2 mL of normal saline every day.

On the first day of the experiment, except the blank control group (Control), the other five groups were challenged with influenza virus by nasal drip after mild anesthesia with ether. Intragastric administration was still performed on the day. The *L. mucosae* intervention group (GDMCC60460) was intragastrically administered with a *L. mucosae* GDMCC60460 suspension diluent containing $10^9$ CFU of bacteria, the *B. breve* CCFM1026 intervention group (CCFM1026) was intragastrically administered with a *B. breve* CCFM1026 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains $5\times10^8$ CFU bacterial amount of *L. mucosae* GDMCC60460 and $5\times10^8$ CFU bacterial amount of *B. breve* CCFM1026), and the other groups (Control, Model and Treatment) were intragastrically administered with 0.2 mL of normal saline every day.

On the second day of the experiment, the drug treatment group with administration of ribavirin (Treatment) was injected intraperitoneally with the drug ribavirin for treatment.

Intragastric administration was continued for 4 days after challenge. The *L. mucosae* intervention group (GDMCC60460) was intragastrically administered with a *L. mucosae* GDMCC60460 suspension diluent containing $10^9$ CFU of bacteria, the *B. breve* CCFM1026 intervention group (CCFM1026) was intragastrically administered with a *B. breve* CCFM1026 suspension diluent containing $10^9$ CFU of bacteria, the bacterial preparation intervention group of the probiotic mixed preparation (GDMCC60460+1026) was intragastrically administered with the probiotic mixed preparation containing $10^9$ CFU of bacteria (the probiotic mixed preparation contains $5\times10^8$ CFU bacterial amount of *L. mucosae* GDMCC60460 and $5\times10^8$ CFU bacterial amount of *B. breve* CCFM1026), and the other groups (Control, Model and Treatment) were intragastrically administered with 0.2 mL of normal saline every day.

The mice were sacrificed after blood collection on the fifth day after challenge. After the mice were sacrificed, the right lung tissues of the mice were taken out and placed in 1 mL of TRIZOL, and cryopreserved in a refrigerator at −80° C. for later use. During extraction, the right lung tissue samples were thawed on ice, and then ground using a DEPC-treated sterile grinder. 200 μL of chloroform was added, the mixture was mixed thoroughly and centrifuged at 4° C. and 12000 rpm for 10 min, and 500 μL of supernatant was removed. An equal volume of isopropanol was added, the mixture was mixed thoroughly and centrifuged at 4° C. and 12000 rpm for 10 min, and the supernatant was removed. 75% ethanol was added for washing RNA once, the mixture was centrifuged at 4° C. and 12000 rpm for 10 min, and the supernatant was removed. After the ethanol evaporated to dryness, 40 μL of DEPC treating water was added to dissolve the RNA. The extracted RNA was cryopreserved in the refrigerator at −80° C. for later use.

A qPCR method was used to determine the relative expression quantity of MxA (the body will react defensively to the influenza virus to clear the invading virus and restore health, MxA is an antiviral protein secreted by the body, which can effectively prevent the virus from replicating), GAPDH was used as the internal reference, a classic $2^{-\Delta\Delta t}$ calculation method was used, and the model group was used as the contrast processing data. The results are shown in FIG. 16.

Figure 16:
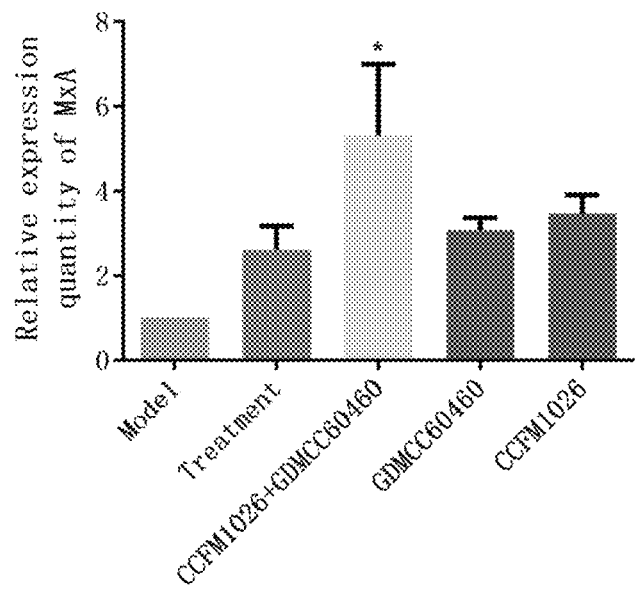
FIG. 16 shows comparison of expression quantity of antiviral protein MxA in lungs of different groups of influenza mice (mixed bacteria).

It can be seen from FIG. 16 that the expression quantity of the antiviral protein MxA in the lungs of mice of the bacterial preparation intervention group (GDMCC60460+ 1026) is the highest and can reach 5.311 times that of the model group, which indicates that the probiotic mixed preparation of the disclosure can effectively participate in the anti-influenza virus process of the body, enhance the expression quantity of the antiviral protein MxA, and help the body to inhibit virus replication. The *B. breve* intervention group (CCFM1026) and *L. mucosae* (GDMCC60460) can also increase the expression quantity of the antiviral protein MxA to a certain extent (the expression quantity is 3.464 and 3.074 times that of the model group, respectively), and the expression quantity is higher than that in the drug treatment group (Treatment), but not as good as that of the mixed bacterial preparation intervention group (GDMCC60460+1026).

EXAMPLE 3-6

Preparation of Solid Beverage Containing Mixed Bacteria

Specific steps are as follows:

*B. breve* CCFM1026 was inoculated into a medium at an inoculation amount of 5-8% of the total mass of the medium, and cultured in an anaerobic environment of 37° C. for 30 h to obtain a culture solution. The culture solution was centrifuged to obtain bacterial cells. The bacterial cells were washed 2-4 times with a phosphate buffer solution with a pH of 7.2, and then resuspended with a 100 g/L trehalose freeze-drying protectant (the mass ratio of the freeze-drying protectant to the bacterial cells is 2:1) to obtain a resuspension solution. The resuspension solution was freeze-dried by vacuum freezing to obtain *B. breve* CCFM1026 bacterial powder.

*L. mucosae* GDMCC60460 was inoculated into a medium at an inoculation amount of 5-8% of the total mass of the medium, and cultured at 37° C. for 18 h to obtain a culture solution. The culture solution was centrifuged to obtain bacterial cells. The bacterial cells were washed 2-4 times with a phosphate buffer solution with a pH of 7.2, and then resuspended with a 100 g/L trehalose freeze-drying protectant (the mass ratio of the freeze-drying protectant to the bacterial cells is 2:1) to obtain a resuspension solution. The resuspension solution was freeze-dried by vacuum freezing to obtain *L. mucosae* GDMCC60460 bacterial powder.

The *L. mucosae* GDMCC60460 bacterial powder and *B. breve* CCFM1026 bacterial powder containing $10^{10}$ CFU of bacteria were respectively mixed with 1 g of maltodextrin to obtain a solid beverage containing the *L. mucosae* GDMCC60460 and the *B. breve* CCFM1026.

10 g of the solid beverage containing the *L. mucosae* GDMCC60460 and the *B. breve* CCFM1026 was taken and redissolved with 20 mL of normal saline. Each mouse was intragastrically administered with 200 microliters of the beverage for two consecutive weeks, which could effectively relieve the symptoms of influenza mice, and had excellent effects on the treatment and/or prevention of influenza.

What is claimed is:

1. A probiotic preparation, comprising a fermentation agent, wherein the fermentation agent comprises *Bifidobacterium breve* (*B. breve*) and *Lactobacillus* mucosae, and wherein the fermentation agent is produced by:

inoculating *B. breve* and *L. mucosae* each separately into an individual medium at an inoculation amount of 5% to 8% of total mass of the medium;

culturing the *B. breve* inoculant in an anaerobic environment at 37° C. for 30 hours, and culturing the *L. mucosae* inoculant at 37° C. for 18 hours, to obtain individual culture solutions of each;

centrifuging the culture solutions to obtain *B. breve* and *L. mucosae* bacterial cell pellets;

washing the bacterial cell pellets 2 to 4 times with a phosphate buffer solution with a pH value of 7.2;

resuspending the bacterial cell pellets in 100 g/L trehalose to obtain individual resuspension solutions; and freeze-drying the resuspension solutions individually by vacuum freezing to obtain *B. breve* and *L. mucosae* bacterial powders; and mixing the obtained *L. mucosae* bacterial powder and the *B. breve* bacterial powder to obtain a fermentation agent, wherein the probiotic preparation comprises the fermentation agent, wherein the *L. mucosae*, is deposited at Guangdong Microbial Culture Collection Center, 5th Floor, Building 59, Grand Courtyard 100, Xianlie Middle Road, Guangzhou, with deposit number GDMCC No. 60460; and wherein the *B. breve* is deposited at Guangdong Microbial Culture Collection Center 5th Floor, Building 59, Grand Courtyard 100, Xianlie Middle Road, Guangzhou, with deposit number GDMCC No. 60459.

2. The probiotic preparation of claim 1, wherein a viable count of *L. mucosae* in the probiotic preparation is not less than $1\times10^6$ CFU/mL; and a viable count of *B. breve* in the probiotic preparation is not less than $1\times10^6$ CFU/mL.

3. A product for treating influenza, comprising the probiotic preparation of claim 1.

4. The product for treating influenza of claim 3, wherein the product comprises food, medicine, or health food.

5. The product for treating influenza of claim 4, further comprising a pharmaceutical carrier or a pharmaceutical excipient.

6. The product for treating influenza of claim 4, wherein the food comprises a dairy product, a bean product, a fruit and vegetable product or a beverage.

7. The product for treating influenza of claim 6, wherein a mass ratio of the trehalose to the bacterial cells is 2:1.

8. The product for treating influenza of claim 3, wherein a pH value of the medium is 6.8.

* * * * *